(12) United States Patent
Lankinen

(10) Patent No.: US 6,616,945 B1
(45) Date of Patent: Sep. 9, 2003

(54) METHOD FOR MAKING A PHARMACEUTICAL FORMULATION

(75) Inventor: Tapio Lankinen, Turku (FI)

(73) Assignee: Leiras Oy, Turku (FI)

(*) Notice: Subject to any disclaimer, the term of this patent is extended or adjusted under 35 U.S.C. 154(b) by 0 days.

(21) Appl. No.: 09/582,370

(22) PCT Filed: Dec. 21, 1998

(86) PCT No.: PCT/FI98/01001
§ 371 (c)(1), (2), (4) Date: Jun. 30, 2000

(87) PCT Pub. No.: WO99/34778
PCT Pub. Date: Jul. 15, 1999

(30) Foreign Application Priority Data

Dec. 31, 1997 (FI) .................................................. 974664

(51) Int. Cl.⁷ ................................................ A61K 9/14
(52) U.S. Cl. .......................................... 424/489; 424/46
(58) Field of Search ......................... 562/496; 424/490, 424/46, 489; 514/826

(56) References Cited

U.S. PATENT DOCUMENTS

| | | | |
|---|---|---|---|
| 5,191,114 A | * 3/1993 | Chen | ........................... 562/496 |
| 5,354,556 A | * 10/1994 | Sparks et al. | ................ 424/419 |
| 5,393,716 A | * 2/1995 | Light et al. | .................. 501/141 |
| 5,503,869 A | 4/1996 | Van Oort | .................... 424/2.14 |
| 5,655,523 A | 8/1997 | Hodson et al. | ............. 128/315 |

FOREIGN PATENT DOCUMENTS

| | | |
|---|---|---|
| GB | 937303 | 9/1963 |
| WO | WO 92/18110 | 10/1992 |
| WO | WO 95/05805 | 3/1995 |

OTHER PUBLICATIONS

Remington's Pharmaceutical Sciences, 16th ed, 1980, p. 203.*

* cited by examiner

Primary Examiner—Edward J. Webman
(74) Attorney, Agent, or Firm—Knobbe Martens Olson & Bear LLP

(57) ABSTRACT

The invention concerns a method for preparing a physically stable and homogeneous powdered preparation containing particles of an active agent. The particles are suspended in a suspending agent in which the particles are insoluble, and the suspending agent is evaporated from the suspension. Physiologically acceptable additives such as a carrier may optionally be added to the suspension.

19 Claims, 2 Drawing Sheets

METHOD FOR MAKING A PHARMACEUTICAL FORMULATION

This application is the U.S. National Phase under 35 U.S.C. §371 of International Application PCT/F198/01001, filed Dec. 21, 1998, which claims priority of Finnish Patent Application No. 974664, filed Dec. 21, 1997.

This invention concerns a method for preparing a physically stable and homogenous powdered preparation containing in particulated form an active agent and optionally conventional physiologically acceptable additives, such as a carrier.

Powder inhalers are widely used for ozone-saving dosing of active drugs into the lungs. These devices can be divided in two categories:
1. Devices provided with a powder reservoir and means for metering a dose from the reservoir for each delivery to the patient
2. Devices provided with pre-metered powder doses in capsules, blisters etc.

The performance of any powder inhaler must fulfill the requirements of Pharmacopeias for delivered dose uniformity (±25% of mean). Also the mass of respirable particles per dose and general stability of the formulation must be documented and accepted by the authorities.

Concerning inhalation, the respirable particles are commonly accepted to be particles having an aerodynamic diameter less than 6 microns, which can be tested in a laboratory.

Dry powders for inhalation are normally manufactured of micron size drug particles and a coarser carrier, e.g. lactose or glucose, by mixing them in a dry homogenizer. All micron size particles are very cohesive and tend to adhere strongly to each other and other surfaces (carrier, container, and the like). Therefore, special care must be paid in the mixing process in order to obtain a homogenous blend. A non-homogenous blend will cause variations in the delivered dose, especially with reservoir devices, which additionally show a natural variation in accuracy of metering the dose.

When a dose is inhaled a part of the micron sized drug particles is separated from the carrier. Only particles this small deposit in the lung. If the forces adhering the drug particles onto other drug particles or carrier particles is increased, the amount of respirable particles will decrease and the clinical effect will be different. Altered adhesion also affects dose metering accuracy in reservoir devices.

A common reason for agglomeration of an inhalation powder is that some substances, often the drug, are in an unstable state. Such instability is mainly caused by polymorphic crystals or amorphous matter, which tend to recrystalize in a thermodynamically most stable state. Simultaneously, micron size particles tend to fuse together and adhere on any available surfaces. Such changes take place slowly at normal room temperatures but are commonly accelerated by elevated temperature, presence of moisture or organic vapours.

Polymorphic crystals may form during crystallization but a proper choice of solvent may prevent it. Amorphous material is normally formed during high-energy treatment of organic solids, e.g. micronization in a jet-mill or ball-mill, or in rapid precipitation with anti-solvent or during spray-drying. Carrier substances may contain amorphous matter as well.

As a summary, a manufacturing method resulting in excellent homogeneity of physically stable substances is well established.

The presence and characteristics of amorphous matter in micronized drug particles has been shown in several publications (e.g. with salbutamol by Ward and Schulz in Pharmaceutical Research, Vol. 12, No 5, 1995).

In WO 95/05805 a micronized drug or a mixture containing a micronized drug is stabilized by using water vapour preferably at 10–50° C. and over 75% relative humidity. This method is useful for water soluble substances. If the mixture contains water insoluble substances, vapour treatment with organic solvents should be carried out, too. Stabilization of dry powder is using vapour and no wet suspension is mentioned. The authors suppose that, as a rule, water soluble substances must be treated with water vapour and water insoluble substances with organic vapour.

In PCT/SE92/00186 a micronized water soluble drug is stabilized in a similar manner with ethanol, acetone or other organic vapours. Prior to the treatment all water was removed from the drug at elevated temperature and under vacuum. After the treatment residues of organic solvent were removed from the drug with an inert gas. No suspension treatment is mentioned.

There are some drawbacks in treating dry powders. During vapour stabilization, the particles obviously tend to fuse together to some extent, which must be controlled. Adequate care must be paid to prevent contamination of drug during the treatment.

Suspension of an active drug in a volatile solvent in making a powder for inhalation is mentioned in U.S. Pat. No. 5,503,869. Here only micronized drug is suspended in HFA-propellants in order to fix an exact dose on a carrier net of metal, plastic, ceramic or similar material. When the propellant is evaporated, the drug can be blown into the air to be inhaled. No stabilization of the drug is mentioned.

BRIEF DESCRIPTION OF THE DRAWINGS

FIG. 1 presents the X-ray diffraction (XRD) patterns of three salbutamol samples.

FIG. 2 presents the X-ray diffraction (XRD) patterns of three samples of Steroid A.

To overcome the drawbacks of the prior art the present invention provides a method for preparing a stable and homogenous dry particulated product which method is characterized in that the particles are suspended in a suspending agent, and from the thus obtained suspension the suspending agent is evaporated.

The other characteristics of the method of this invention are revealed in the claims 2–13.

The invention also concerns the product obtained by the method of this invention. The product is stable for longer periods and the particulate material is homogenous.

Attempts to manufacture a lactose blend containing only 0.5 percents of an active drug by dry mixing failed because it was not possible to obtain a totally homogenous mixture of the ingredients by dry-mixing. It was found that the formulation always contained some agglomerates of the active drug, which spoiled the delivered dose uniformly in a reservoir powder inhaler. However, by mixing the ingredients as a n-hexane suspension aided by sonic treatment, a totally homogeneous blend was obtained after evaporation of heptane on a water bath.

When this method was used to make a formulation of salbutamol sulphate and lactose, a homogenous formulation was obtained, but its stability was not satisfactory; the drug particles agglomerated to an unacceptable level at room temperature for six months.

One test formulation was left at room temperature as heptane suspension over the weekend in a glass bottle, followed by evaporation of heptane on a water bath.

Surprisingly, it was found later that this formulation remained stable for over two years at room temperature. Apparently the prolonged suspension state stabilized the formulation probably due to physical changes in the active substance.

EXAMPLE 1
Tests with Salbutamol Sulphate

Three samples of micronized salbutamol sulphate were stirred 7 hours at 50, 60 and 70° C. as n-heptane suspension. Then the solvent was evaporated in vacuum.

Röntgendiffraction (XRD) studies suggested that a detectable amount of the drug was amorphous in the untreated sample but could be recrystallized during the treatment. Seven hours at 60 and 70° C. resulted in practically total crystallinity and slightly less at 50° C.

When a sample of micronized drug was stored 10 hors at 40° C. and 50% relative humidity (RH), a clear decrease took place in the amount of amorphous matter. XRD patterns of three samples are shown in FIG. 1.

Figure 1:
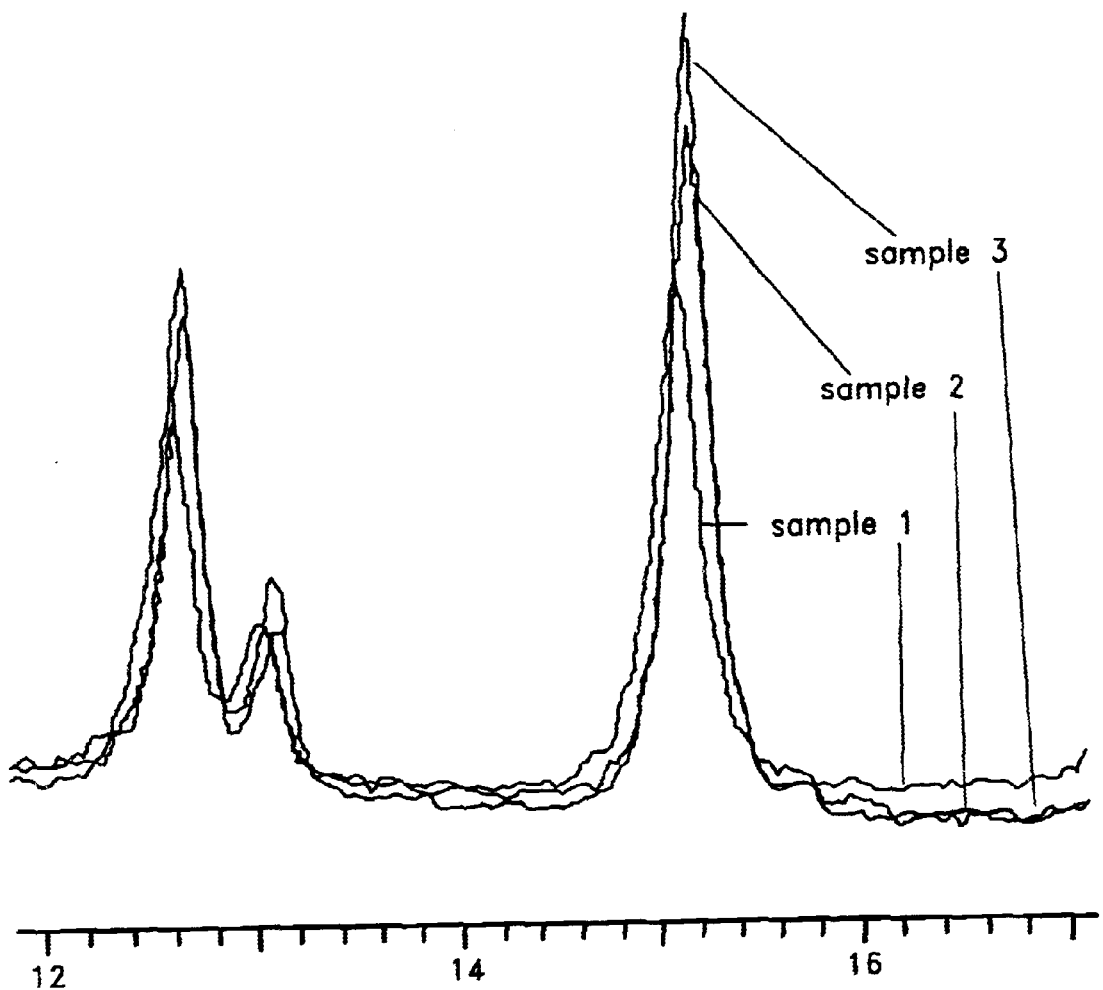

In FIG. 1, the XRD patterns of the three salbutamol samples, which were each treated differently before analysis is shown as follows:
1=micronized
2=stored 100 hours at 40° C., 50% RH
3=stirred 7 hours at 70° C. as n-heptane suspension.

Microcalorimetric (IMC) studies verified good stability of the treated samples in presence of moisture. The untreated sample was clearly unstable, especially at a RH of over 50%.

EXAMPLE 2
Preparing a Salbutamol Formulation

Micronized salbutamol sulphate was suspended in n-hexane to a thin slurry, aided by gentle sonic treatment at room temperature. Lactose (325 mesh) was added during mechanical stirring. The suspension was stirred some hours at 50° C., followed by evaporation of the solvent in a rotating evaporator. A well-flowing powder was the result.

Homogeneity of the drug in the formulation was extremely good, showing RSD values for 2 mg samples of only 1–3%.

Characteristics for this formulation, when used with a model reservoir device, are:

| | |
|---|---|
| Respirable fraction in delivered dose | 0.4–0.6 |
| RSD % for delivered dose uniformity | <10 |
| Stability at room circumstances | over 2 years |
| Stability at 40° C./75% RH | over ½ years |

The characteristics are repeatable from batch to batch and the method has been scaled up for production.

EXAMPLE 3
Tests with the experimental steroid A

Attempts to make a lactose blend of a n-hexane suspension method at room temperature failed because the particle size of the active drug in the delivered dose increased within weeks to an unacceptable level.

XRD studies suggested large differences in micronized and unmicronized materials, obviously due to different amorphous contents.

Freshly micronized drug showed no sharp diffraction patterns which indicates very high amorphous content. When stored at room temperature for some months, a considerable fraction of the amorphous matter had been recrystallized. Also the initial mean particle size had been increased close to the upper acceptable limit.

Samples of some months ago micronized material were suspended in n-heptane and stirred 7 and 16 hours at 70° C., followed by drying. XRD- and IMC-studies confirmed total recrystallization of both samples.

Figure 2:
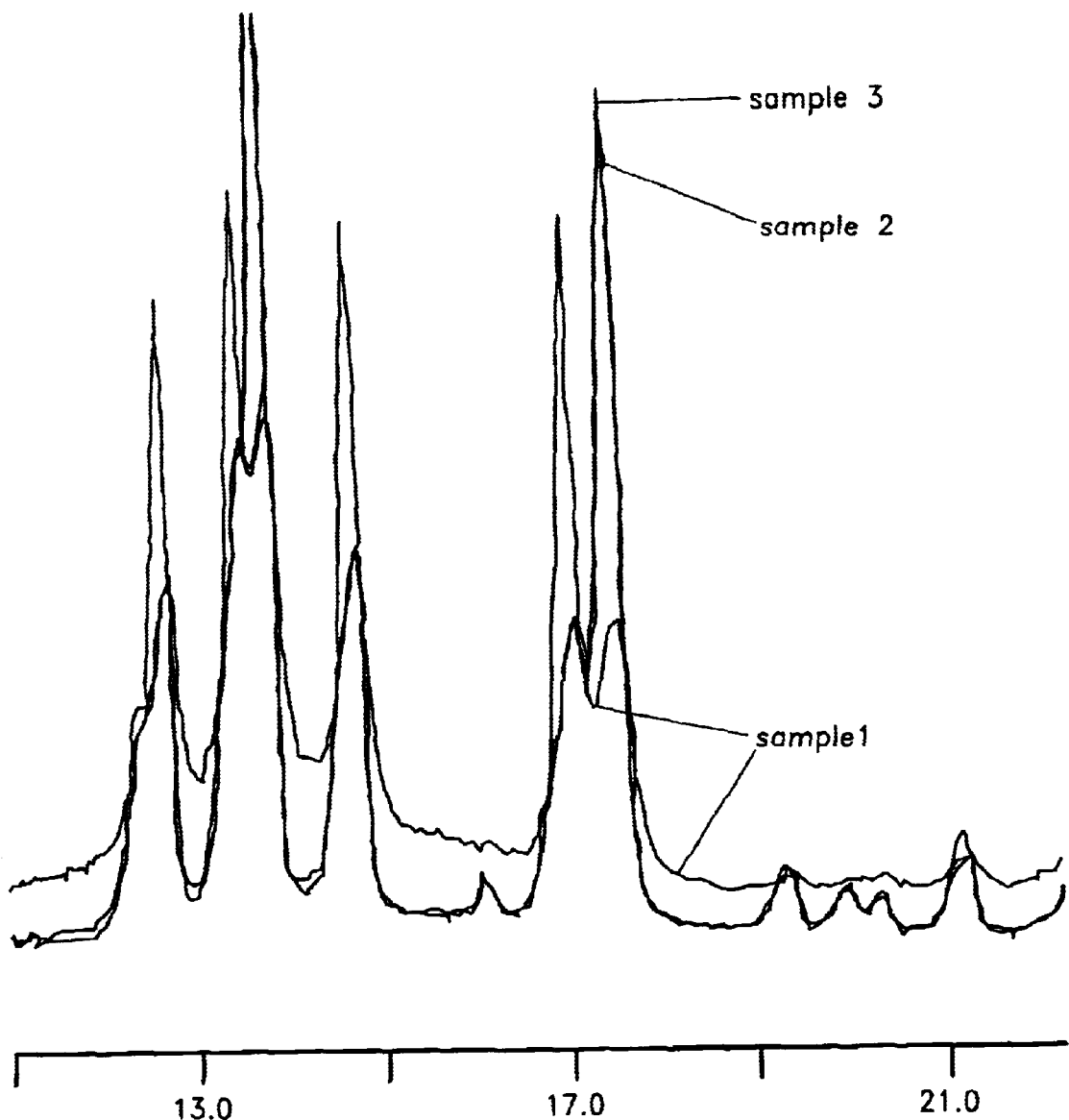

XRD patterns of three samples are shown in FIG. 2.

In FIG. 2, the XRD patterns of three samples of Steroid A, which were each treated differently before analysis is shown as follows:
1=micronized
2=stored 100 hours at 40° C., 50% RH
3=stirred 7 hours at 70° C., as n-heptane suspension.

EXAMPLE 4
Preparing a Formulation of Steroid A

The suspension of the drug in n-heptane was stirred 16 hours at 70° C. Than lactose was added during stirring. The solvent was removed by vacuum in a rotatory evaporator. As a result, free flowing dry powder was obtained. Stability of the formulation was studied in extreme conditions (40° C./75% RH) by metering the small particle fraction in the delivered dose, when the model reservoir device was used. No change in the particle size distribution or respirable fraction in the delivered dose could be seen, when tested after 2 and 4 weeks. The results indicate superb stability of the formulation compared to earlier attempts with untreated micronized drug.

EXAMPLE 5
Tests with the Experimental Steroid B

Four samples of micronized drug were treated in heptane-ethanol (96:4) and dried:
1. mixing 30 minutes at room temperature
2. mixing 7 hours at room temperature
3. mixing 30 minutes at 50° C.
4. mixing 7 hours at 50° C.

XRD-studies revealed no large differences between the samples. However, the untreated drug showed the lowest peak height which suggests the largest amorphous content. Specific surface area and the energy for moisture absorption during transfer from 0 to 80% RH were metered:

| | Area $m^2/g$ | $\Delta H$ $J/m^2$ |
|---|---|---|
| Micronized, untreated | 6.55 | 1.21 |
| Sample 1 | 6.17 | 0.95 |
| 2 | 5.30 | 0.99 |
| 3 | 5.69 | 0.94 |
| 4 | 5.38 | 1.00 |

The differences are small but indicate that a physical change took place during the treatment and the treated samples are in a more stable state compared to the untreated sample. The overall results encourage to use suspension stabilization using short treatment at normal or slightly elevated temperature.

Further experiences and clarifications on the method

Budesonide and three experimental drugs for inhalation have been formulated using the suspension mixing method. Coarse lactose or glucose was used as the carrier and the drug-carrier ratios varied between 1:200 and 50:100. N-alkane alone or mixed with a small amount of ethanol or methanol was used as suspending agent. In all cases short mixing times were used, followed by removal of the suspending agent in a rotating evaporator. Budesonide formulation showed excellent homogeneity and stability; no changes in the particle parameters have been found at room circumstances within one year.

The formulations of the three experimental drugs showed excellent homogeneity and acceptable stability.

The suspending method is a very useful method for homogenizing, even if all of the ingredients were in a stable state. If not stable, it is easy to increase the mixing time and/or mixing temperature and monitor the results by physical methods instead of timely stability tests. During this stabilization, the essential benefit of the suspension method is that the liquid prevents agglomeration of the particles during recrystalization.

The manufacturing process can be done in a totally closed system in absence of water. The process is very safe in respect to any contamination and can be used in large-scale production. The mixing vessel can be equipped with mechanical stirrer, ultrasonic transmitter, heating and filtering means and vacuum evaporation so that the formulation is ready to use after the process.

There seems to be no other limitations concerning the suspending agent, but it must be chemically inert in respect of the formulation components, fairly volatile and the components must be practically insoluble in the suspending agent. N-alkanes are ideal in most cases. Small amounts of methaol, ethanol, acetone, and the like, may be used to improve wetting of the powders. Even absolute ethanol and halogenated hydrocarbons, such as CFC 11 and HFC 227, have been used successfully in making a salbutamol sulphate—lactose monohydrate formulation.

If heat treatment is used, it can be conducted separately for the drug and the carrier or jointly for the drug, carrier and other possible ingredients concerned. It is preferred to treat both the drug and the carrier, because also the carrier may contain unstable matter and cause formulation changes during storage. As shown with salbutamol, some hours mixing in n-hexane at 50° C. will produce a practically stable formulation.

What is claimed is:

1. A method for preparing a physically stable and homogenous powdered pharmaceutical preparation to be inhaled comprising particles of a pharmaceutical and at least one physiologically acceptable additive, said method comprising:

- suspending particles of said preparation in a suspending agent, thereby forming a suspension, wherein the particles are essentially insoluble in the suspending agent, and;
- evaporating the suspending agent from the suspension, wherein said particles comprise the particles preparation and the carrier in admixture.

2. A method according to claim 1, wherein the suspending agent is selected from the group consisting of: alkanes, alcohols, ketones and mixtures thereof.

3. A method according to claim 2, wherein the suspending agent is selected from the group consisting of: an alkane, preferably n-hexane or heptane, an alcohol, and a halogenated hydrocarbon.

4. A method according to claim 1 wherein the suspended particles are deagglomerated and/or homogenized by stirring.

5. A method according to claim 1, further comprising ultrasonic treatment of the suspension.

6. A method according to claim 1, wherein the suspension is stored for a time sufficient to allow contact between the particles and the suspending agent before evaporation.

7. A method according to claim 1, wherein the suspension is stored for a time between about 3 minutes and 5 days.

8. A method according to claim 1, wherein said suspending is at a temperature of greater than about room temperature.

9. A method according to claim 8, wherein said temperature is between about 40° C. and about 90° C.

10. A method according to claim 1, wherein the active agent is an organic compound containing an amorphous substance.

11. A method according to claim 10, wherein the active agent is salbutamol.

12. A method according to claim 1, wherein the active agent is a steroid.

13. A method according to claim 1, wherein the active agent is budesonide.

14. The product obtained by the method according to claim 1.

15. The method according to claim 3, wherein the alkane is selected from the group consisting of n-hexane and n-heptane.

16. The method of claim 3, wherein said alcohol is methanol or ethanol.

17. The method according to claim 7, wherein the suspension is stored for about 3 hours.

18. The method according to claim 9, wherein said temperature is between about 40° C. and about 70° C.

19. The method according to claim 9, wherein said temperature is between about and 50° C. and about 70° C.

* * * * *